(12) United States Patent
Salamitou et al.

(10) Patent No.: US 10,960,157 B2
(45) Date of Patent: Mar. 30, 2021

(54) OXYGEN THERAPY MONITORING DEVICE AND METHOD

(71) Applicant: SRETT (SAS), Boulogne Billancourt (FR)

(72) Inventors: Philippe Salamitou, Boulogne Billancourt (FR); Xuan Loc Le, Boulogne Billancourt (FR)

(73) Assignee: SRETT (SAS), Boulogne Brillancou (FR)

( * ) Notice: Subject to any disclaimer, the term of this patent is extended or adjusted under 35 U.S.C. 154(b) by 205 days.

(21) Appl. No.: 15/760,102

(22) PCT Filed: Sep. 22, 2016

(86) PCT No.: PCT/EP2016/072559
§ 371 (c)(1),
(2) Date: Mar. 14, 2018

(87) PCT Pub. No.: WO2017/050908
PCT Pub. Date: Mar. 30, 2017

(65) Prior Publication Data
US 2018/0250481 A1    Sep. 6, 2018

(30) Foreign Application Priority Data

Sep. 22, 2015 (EP) .................. 15306473

(51) Int. Cl.
*A61M 16/00* (2006.01)
*A61B 5/08* (2006.01)
(Continued)

(52) U.S. Cl.
CPC ......... *A61M 16/0003* (2014.02); *A61B 5/087* (2013.01); *A61B 5/0816* (2013.01);
(Continued)

(58) Field of Classification Search
CPC .............. A61M 16/00; A61M 16/0003; A61M 16/024; A61M 16/0666; A61M 16/0672;
(Continued)

(56) References Cited

U.S. PATENT DOCUMENTS 3,690,171 A * 9/1972 Tippetts ................ G01F 1/3227
73/861.19
5,298,886 A * 3/1994 Ueki ..................... G01F 1/3227
340/606
(Continued)

FOREIGN PATENT DOCUMENTS

EP      2390632 A1 * 11/2011 ........... G01F 1/3281
WO 2013042071 A1    3/2013
(Continued)

OTHER PUBLICATIONS

Hardinge M, et al., "British Thoracic Society guidlines for home oxygen use in adults," Journal Thorax, Jun. 2015, vol. 70, Supplement 1.
(Continued)

*Primary Examiner* — Joseph D. Boecker
(74) *Attorney, Agent, or Firm* — Karceski IP Law, PLLC

(57) ABSTRACT

An oxygen therapy monitoring device includes an oscillation chamber with in a gas flow path adapted to pass a gas flow from a source to a breathing interface for a person. The oscillation chamber induces an oscillation in the gas flow that varies as a function of a flow rate of the gas flow. A measurement arrangement measures the oscillation induced in the gas flow and determines the flow rate on the basis of the oscillation that is measured.

10 Claims, 5 Drawing Sheets

(51) Int. Cl.
  *A61B 5/097* (2006.01)
  *G01F 1/32* (2006.01)
  *A61B 5/087* (2006.01)
  *A61M 16/10* (2006.01)

(52) U.S. Cl.
  CPC ........... *A61B 5/097* (2013.01); *A61M 16/024* (2017.08); *A61M 16/1005* (2014.02); *G01F 1/3227* (2013.01); *A61B 2560/04* (2013.01); *A61M 16/10* (2013.01); *A61M 2016/0027* (2013.01); *A61M 2016/0039* (2013.01); *A61M 2202/0208* (2013.01); *A61M 2205/0244* (2013.01); *A61M 2205/3375* (2013.01); *A61M 2205/50* (2013.01); *A61M 2205/52* (2013.01)

(58) Field of Classification Search
  CPC .......... A61M 16/0677; A61M 16/1005; A61M 2016/0027; A61M 2016/003; A61M 2016/0033; A61M 2016/0039; A61M 2016/10; A61M 2016/102; A61M 2202/0208; A61M 2205/0244; A61M 2205/3334; A61M 2205/3375; A61B 5/0816; A61B 5/087; A61B 5/097; A61B 2560/04; G01F 1/3227; F15C 1/22
  See application file for complete search history.

(56) References Cited

U.S. PATENT DOCUMENTS

| | | | | |
|---|---|---|---|---|
| 5,864,067 A | * | 1/1999 | Ligneul | F15C 1/22 73/861.21 |
| 5,959,216 A | * | 9/1999 | Hocquet | G01F 1/3227 73/861.19 |
| 6,250,132 B1 | * | 6/2001 | Drzewiecki | A61M 16/0051 73/23.2 |
| 6,644,311 B1 | * | 11/2003 | Truitt | A61M 16/0069 128/204.18 |
| 2006/0100537 A1 | * | 5/2006 | Williams | A61B 5/087 600/538 |
| 2007/0239058 A1 | * | 10/2007 | Krasilchikov | A61B 5/087 600/538 |
| 2011/0083516 A1 | * | 4/2011 | Vaidya | G01F 1/3227 73/861.61 |
| 2011/0094308 A1 | * | 4/2011 | Vaidya | G01F 1/3227 73/861.19 |
| 2012/0232420 A1 | * | 9/2012 | Salamitou | A61B 5/087 600/538 |
| 2013/0032142 A1 | | 2/2013 | Neely | |
| 2013/0317379 A1 | * | 11/2013 | Brimer | A61B 5/087 600/538 |
| 2018/0066968 A1 | * | 3/2018 | Ammouri | A61B 5/087 |

FOREIGN PATENT DOCUMENTS

| | | |
|---|---|---|
| WO | 2013070545 A1 | 5/2013 |
| WO | 2015130717 A2 | 9/2015 |

OTHER PUBLICATIONS

International Search Report and Written Opinion dated Dec. 9, 2016, for International Patent Application No. PCTEP2016/072559.
International Preliminary Report on Patentability dated Dec. 1, 2017, for International Patent Application No. PCTEP2016/072559.

* cited by examiner

US 10,960,157 B2

OXYGEN THERAPY MONITORING DEVICE AND METHOD

CROSS-REFERENCE TO RELATED APPLICATION(S)

This is a National Stage Entry into the United States Patent and Trademark Office from International PCT Patent Application No. PCT/EP2016/072559, having an international filing date of Sep. 22, 2016, which claims priority to European Patent Application No. EP 15306473.8, filed on Sep. 22, 2015, the entire contents of both of which are incorporated herein by reference.

FIELD OF THE INVENTION

An aspect of the invention relates to an oxygen therapy monitoring device. The oxygen therapy monitoring device may be used in, for example, long-term oxygen therapy and ambulatory oxygen therapy. Other aspects of the invention relate to an oxygen therapy monitoring system and to a non therapeutic method of monitoring an oxygen therapy applied to a person.

BACKGROUND OF THE INVENTION

The journal "Thorax", June 2015, Volume 70, Supplement 1, presents BTS guidelines for home oxygen use in adults, BTS being an acronym of "British Thoracic Society". Long-term oxygen therapy (LTOT) can be defined as oxygen used for at least 15 hours per day in chronically hypoxaemic patients. A recommendation states that LTOT should be ordered for a minimum of 15 hours per day, and up to 24 hours per day may be of additional benefit.

Flow rates in LTOT are discussed. A flow rate based on a single measure of oxygenation at rest may not necessarily guarantee adequate oxygenation dining day-to-day activities where oxygen requirements may fluctuate. Individual tailoring of flow rates to suit patients' requirements during exercise, rest and sleep can reduce median oxygen flow rate from 2.5 to 1.2 L/min, while the percentage of time SpO2 was within the target range increased from 24.8% to 52.8% (p=0.001).

The patent application published under number US 2006/0100537 A1 describes a spirometer for measuring fluid flow, particularly associated with exhalation of respiratory patients. The spirometer has a fluidic oscillator wherein the fluid oscillates within a chamber of the fluidic oscillator, An oscillation frequency of the fluid flow within the chamber is correlated to a flow rate. A computer is used to process input data, such as data representing frequency of the oscillatory flow within the chamber, to a flow rate passing through the spirometer.

SUMMARY OF THE INVENTION

There is a need for a non therapeutic technique that allows monitoring an oxygen therapy, which is applied to a person.

In order to better address this need, in accordance with an aspect of the invention, there is provided an oxygen therapy monitoring device as defined in claim 1, which is appended to the description. This oxygen therapy monitoring device allows a relatively precise flow rate measurement at relatively low power consumption. Moreover, the device can be relatively small, lightweight, and, therefore, portable.

Another aspect of the invention concerns an oxygen therapy monitoring system that comprises an oxygen therapy monitoring device as defined in claim 1, and a station adapted to collect measured data from the oxygen therapy monitoring device. Yet another aspect of the invention concerns a non therapeutic method of monitoring an oxygen therapy applied to a person, the non therapeutic method comprising a step of collecting measured data from an oxygen therapy monitoring device as defined in claim 1.

Yet another aspect of the invention concerns a non therapeutic method in which a flow rate is measured of a gas flow from a source to a breathing interface for a person, as well as an overpressure in the gas flow at the breathing interface, in which the overpressure is divided by the flow rate of the gas flow so as to obtain a resistance value, and in which a breathing characteristic is determined on the basis of a sequence of successive resistance values that have been obtained. It should be noted that this non therapeutic method does not necessarily require an oxygen therapy monitoring device as defined in claim 1.

Yet another aspect of the invention concerns a computer program product comprising a set of instructions that enables a processor, which is capable of executing the set of instructions, to carry out the non therapeutic method defined in the preceding paragraph.

An embodiment of the invention may comprise one or more additional features defined in the dependent claims, which are appended to the description.

For the purpose of illustration, a detailed description of some embodiment of the invention is presented with reference to accompanying drawings.

DETAILED DESCRIPTION

Figure 1:
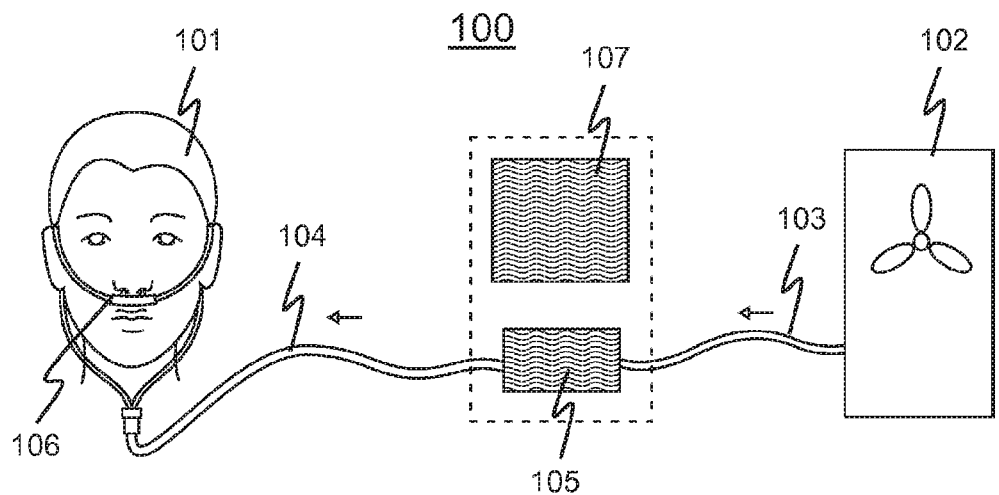
FIG. 1 is a block diagram of an oxygen therapy monitoring system.

FIG. 1 schematically illustrates a system for monitoring an oxygen therapy that is applied to a person 101. The system 100 is represented in a block diagram. The system 100 may be used, for example, in an oxygen therapy method, or an ambulatory oxygen therapy method that is applied to a person 101, who is also represented in FIG. 1.

The system 100 comprises a gas source 102, various tubes 103, 104, an oxygen therapy monitoring device 105, and a breathing interface 106 for the person 101 who can receive breathable gas though the system 100. The gas source 102 may be in the form of, for example, a gas cylinder or an oxygen concentrator. The breathing interface 106 may be in the form of, for example, a breathing mask or a nasal cannula. The breathing interface 106 will be referred to hereinafter as "mask 106" for reasons of convenience and conciseness.

The system 100 may further comprise an in-situ station 107 for collecting data from the oxygen therapy monitoring device 105, or for transferring this data to a remote data collection entity, or both. The oxygen therapy monitoring device 105 and the in-situ station 107 may each comprise a wireless communication interface so that a wireless data communication can be established between these entities. Data from the oxygen therapy monitoring device 105 thus may be locally stored, in-situ, or may be send to a remote data collection entity, or both.

The system 100 basically operates as follows. The gas source 102 provides a flow of breathable gas, which may be relatively rich of oxygen. The gas flow passes through a tube 103, the oxygen therapy monitoring device 105, and another tube 104 and reaches the mask 106. The person 101 receives the gas flow though the mask 106 and can thus breathe the breathable gas that originates from the gas source 102. The gas flow may have a flow rate in a range between, for example, 0.5 liter per minute (Lpm) and 10 Lpm. This is a typical flow range for oxygen therapy.

The gas source 102 may be set to provide the gas flow at a specific target flow rate, which may be prescribed by a physician. However, in practice, the gas flow may have a flow rate that deviates to a certain extent from the specific target flow rate. This deviation may be static, or dynamic, or both. For example, the deviation may, at least partially, be in the form of an oscillation that is caused by a flow rate control loop associated with, or comprised in, the gas source 102.

The oxygen therapy monitoring device 105 measures a pressure of the gas flow that is applied to the person 101. In addition, the oxygen therapy monitoring device 105 measures the flow rate of the gas flow, which may deviate from the specific target flow rate as explained hereinbefore. These measured physical quantities of the gas flow, the pressure and the flow rate, can be used, for example, to monitor whether a prescribed treatment is effectively and correctly applied by the system 100, or not. In addition, the measured physical quantities may be used to determine a breathing characteristic of the person 101. Accordingly, the system 100 may provide health state information with regard to the person 101 who breathes through the system 100, at least partially.

Figure 2:
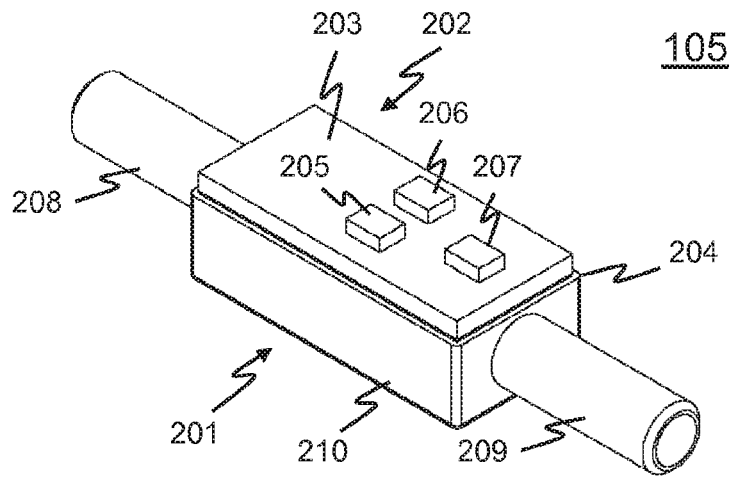
FIG. 2 is a schematic perspective view of an oxygen therapy monitoring device that forms part of the oxygen therapy monitoring system.

FIG. 2 schematically illustrates the oxygen therapy monitoring device 105. FIG. 2 provides a schematic perspective view of the oxygen therapy monitoring device 105. The oxygen therapy monitoring device 105 comprises a gas flow passage module 201 and a measurement arrangement 202, which may be implemented on a printed circuit board 203, as illustrated in FIG. 2. An acoustically transparent membrane 204 may be disposed between a top wall of the gas flow passage module 201 and the printed circuit board 203.

The oxygen therapy monitoring device 105 may further comprise a housing and a battery. The battery may be comprised in the housing together with the other aforementioned parts of the oxygen therapy monitoring device 105. The housing and the battery are not shown in FIG. 2 for reasons of convenience and simplicity. The oxygen therapy monitoring device 105 may be portable and low-power, requiring no coupling to an external electrical energy source in order to operate.

The measurement arrangement 202 comprises a pair of acoustic transducers 205, 206 and a pressure sensor 207, which are mounted on the printed circuit board 203. One of the acoustic transducers 205 will be referred to as first acoustic transducer 205 hereinafter, and the other acoustic transducer 206 will be referred to as second acoustic transducer 206 for reasons of convenience and clarity.

The first acoustic transducer 205 may be in the form of a MEMS microphone, which consumes relatively little power and has favorable transducer characteristics, in particular in terms of sensitivity and speed. For example, a MEMS microphone may operate at a supply voltage of 3.0 V, consuming 10 to 20 µA only, while transducing acoustic signals in a frequency range comprised between 50 Hz and 20 kHz with relatively high sensitivity. The second acoustic transducer may also be in the form of a MEMS microphone. The pressure sensor 207 may also of a MEMS type sensor, which provides a digital output and which may communicate with a microprocessor using I2C protocol.

The gas flow passage module 201 comprises an inlet connector 208 and an outlet connector 209 at opposite sides of a main body 210. These connectors 208, 209 are preferably adapted to engage with standard tubes used in oxygen therapy, which may have a diameter of approximately 6 mm. Referring to FIG. 1, the inlet connector 208 engages with the tube 103 that couples the oxygen therapy monitoring device 105 to the gas source 102. The outlet connector 209 engages with the other tube 104 that couples the oxygen therapy monitoring device 105 to the mask 106. Accordingly, the gas flow passage module 201 defines a gas flow path that passes the gas flow from the gas source 102 to the mask 106 that is worn by the person 101 illustrated in FIG. 1.

The inlet connector 208 is preferably arranged to relatively easily establish a sealed connection with a tube and to then hold the tube firmly enough in order to prevent accidental disconnection. To that end, the inlet connector 208 may comprise a front end having a ribbed outer surface formed by a series of conical sections, whereby such a section has an outer diameter that increases in a direction towards the main body 210 of the gas flow passage module 201. The inlet connector 208 may further comprise a stopper element that defines an end position for a tube that engages with the connector. The outlet connector 209 may be arranged similarly, in a symmetrical fashion. The aforementioned details of the inlet connector 208 and the outlet connector 209 are not shown in FIG. 2 for reasons of convenience and simplicity.

Figure 3:
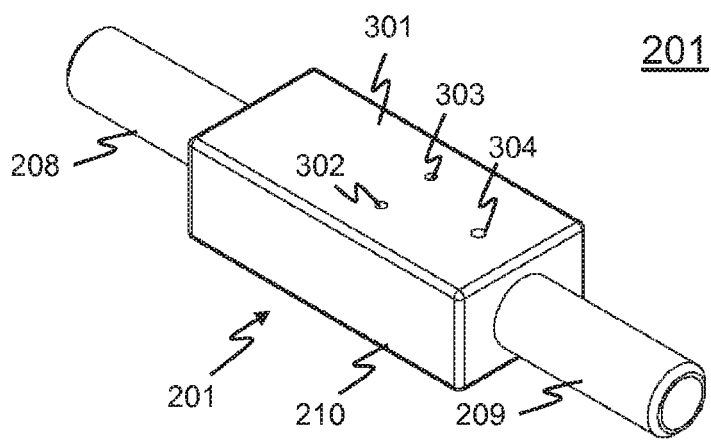
FIG. 3 is a schematic perspective view of a gas flow passage module that forms part of the oxygen therapy monitoring device.
Figure 4:
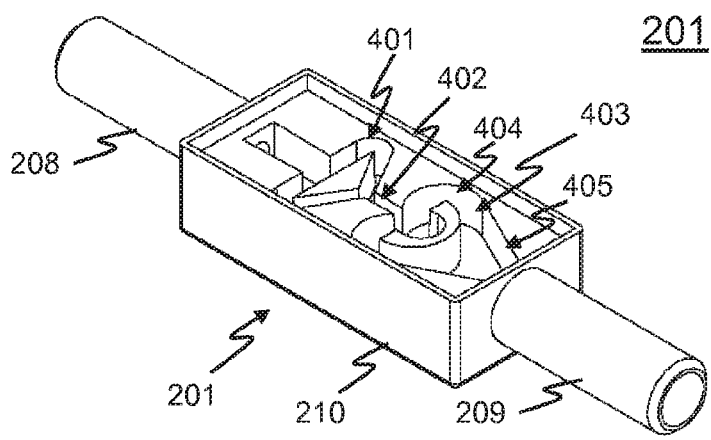
FIG. 4 is another schematic perspective view of the gas flow passage module whereby a top wall has been omitted so that an interior structure is visible.

FIGS. 3 and 4 schematically illustrate the gas flow passage module 201. FIG. 3 provides a schematic perspective view of the gas flow passage module 201. In FIG. 3, the top wall of the gas flow passage module 201 is visible and denoted by reference numeral 301. FIG. 4 provides another schematic perspective view of the gas flow passage module 201 whereby the top wall 301 has been omitted so that an interior structure is visible.

FIG. 4 shows that the gas flow passage module 201 comprises various successive sections from the inlet connector 208 to the outlet connector 209. These sections include a flow conditioner 401, a nozzle 402, and an oscillation chamber 403. The oscillation chamber 403 has a vortex inducing section 404 and an output section 405. The oscillation chamber 403 may have a volume smaller than 1000 mm$^3$. The volume of the oscillation chamber 403 is related to measuring the flow rate. This will be discussed in greater detail hereinafter.

FIG. 3 shows that the top wall 301 of the gas flow passage module 201 comprises various bores 302, 303, 304. These bores 302, 303, 304 may be regarded as pressure taps and will hereinafter be referred to as pressure taps for reasons of convenience and illustration. A first pressure tap 302 extends from an exterior side of the top wall 301 to a first location in the vortex inducing section 404 of the oscillation chamber 403. A second pressure tap 303 extends from the exterior side to a second location in the vortex inducing section 404 of the oscillation chamber 403. A further, third pressure tap 304 extends from the exterior side into the output section 405 of the oscillation chamber 403. The third pressure tap 304 may centrally be located on a longitudinal symmetry axis of the gas flow passage module 201. The first and second pressure taps 302, 303 may be symmetrically located with respect to this longitudinal symmetry axis.

The printed circuit hoard 203 also comprises various bores that are aligned with the pressure taps 302, 303, 304 in the gas flow passage module 201. These bores are not visible in the drawings, but will be described hereinafter. A first bore in the printed circuit board 203 is located beneath the first acoustic transducer 205 shown in FIG. 2. This bore is aligned with the first pressure tap 302 shown in FIG. 3. Accordingly, the first bore provides a pressure communication between the first location in the vortex inducing section 404 of the oscillation chamber 403 and the first acoustic transducer 205. A second bore in the printed circuit board 203 is located beneath the second acoustic transducer 206 shown in FIG. 2. This bore is aligned with the second pressure tap 303 shown in FIG. 3. Accordingly, the second bore provides a pressure communication between the second location in the vortex inducing section 404 of the oscillation chamber 403 and the second acoustic transducer 206. A third bore in the printed circuit board 203 is located beneath the pressure sensor 207 shown in FIG. 2. This bore is aligned with the third pressure tap 304 shown in FIG. 3. Accordingly, the third bore provides a pressure communication between the third location in the vortex inducing section 404 of the oscillation chamber 403 and the pressure sensor 207.

Figure 5:
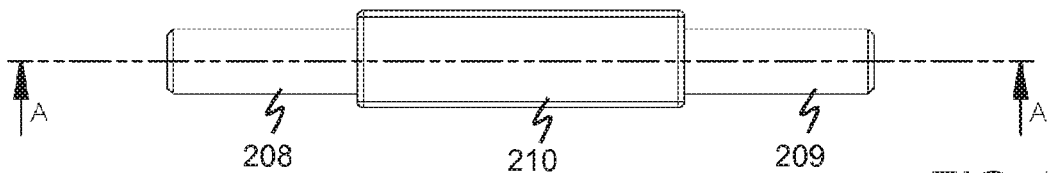
FIG. 5 is a schematic side view of the gas flow passage module in which a (longitudinal) cut line A-A is indicated.
Figure 6:
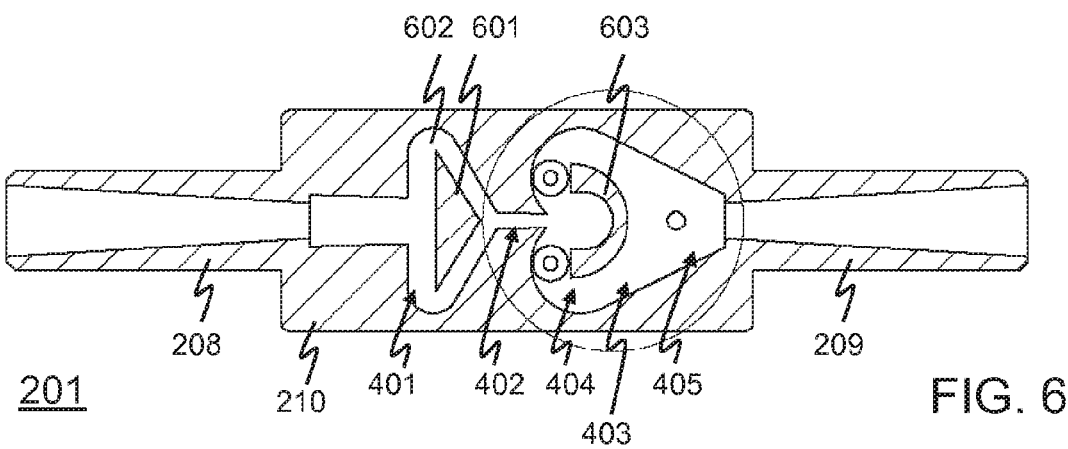
FIG. 6 is a schematic cut (cross sectional) view of the gas flow passage module along the cut line A-A indicated in FIG. 5.
Figure 7:
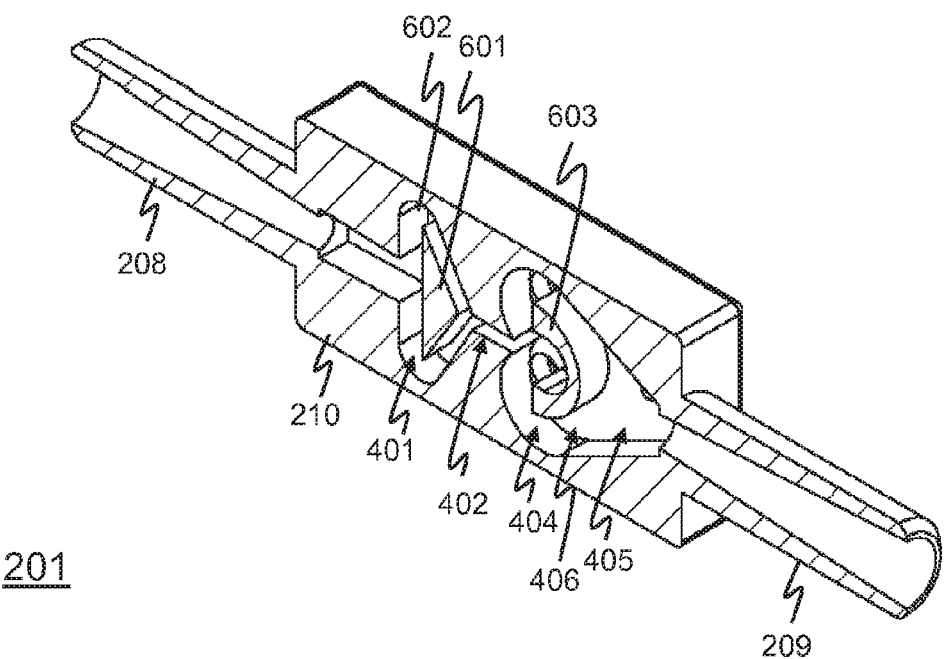
FIG. 7 is a schematic perspective cut view of the gas flow passage module along the cut line A-A indicated in FIG. 5.

FIGS. 5, 6, and 7 further schematically illustrate the gas flow passage module 201. FIG. 5 provides a schematic side view of the gas flow passage module 201. In FIG. 5, a (longitudinal) cut line A-A is indicated. FIG. 6 provides a schematic cut (cross sectional) view of along the cut line A-A indicated in FIG. 5. FIG. 7 provides a schematic perspective cut view of along the cut line A-A indicated in FIG. 5.

The flow conditioner 401 comprises a triangularly shaped element 601 in a triangularly shaped cavity 602. In the cut view of FIG. 6, the triangularly shaped element 601 constitutes an obtuse isosceles triangle. A largest side of this triangle faces the inlet connector 208. The triangularly shaped cavity 602 has two rounded acute angles. These angles may each have a radius of curvature comprised between, for example, 1 and 2 mm, 1.5 mm being a suitable value. The triangularly shaped element 601 may also have two rounded acute angles, although FIGS. 6 and 7 show sharp acute angles for reasons of convenience and simplicity. The two rounded acute angles of the triangularly shaped. element 601 may each have a radius of curvature comprised between, for example, 0.1 and 0.3 mm, 0.2 mm being a suitable value. The radius of curvature of a rounded acute angle of triangularly shaped cavity 602 may have an origin that is aligned with the origin of the radius of curvature of the rounded acute angle of the triangularly shaped element 601 that faces the rounded acute angle of the triangularly shaped cavity 602. In this way, the aforementioned rounded acute angles define a passage of constant section.

The nozzle 402 may have a slightly convergent profile. The angle of convergence may be comprised between, for example, and 1° and 2°, 1.45° being a suitable value. The nozzle 402 may have a slot-shaped tip that ends in the oscillation chamber 403. An inlet end of this tip may have a width comprised between, for example, 0.6 and 1.2 mm, 0.9 mm being a suitable value. An outlet end of this tip, in the oscillation chamber 403, may have a width comprised between, for example, 0.4 and 1.0 mm, 0.7 mm being a suitable value. The tip may have an angle of convergence comprised between, for example, 38 and 45°, 41.5° being a suitable value.

The oscillation chamber 403 comprises a gas flow obstacle element 603, This element defines a cavity facing the nozzle 402 through which the gas flow enters the oscillation chamber 403. The gas flow obstacle element 603 has a semicircular shape, that is, a form of half a circle. The gas flow obstacle element 603 may have a semicircular inner side that has a radius of curvature comprised between, for example, 1.0 and 2.2 mm, 1.6 mm being a suitable value. A semicircular outer side may have a radius of curvature comprised between, for example, 2.4 and 4.0 mm, 3.2 mm being a suitable value.

The vortex inducing section 404 of the oscillation chamber 403 may be kidney shaped as illustrated in, for example, FIGS. 6 and 7. That is, the oscillation chamber 403 may comprise a kidney shaped cavity in which the gas flow obstacle element 603 is present. At least a part of this cavity is delimited by curved walls, which may have a radius of curvature comprised between, for example, 2 and 3.5 mm, 2.75 mm being a suitable value. The output section 405 of the oscillation chamber 403 may have a converging funnel-like shape as illustrated in, for example, FIGS. 6 and 7. The output section 405 may have a converging angle comprised between, for example, 20° and 30°, 25° being a suitable value.

The oscillation chamber 403 can be regarded as having a closed configuration. Oscillation chambers that have an open configuration typically do not comprise an element comparable with the gas flow obstacle element 603 shown in FIGS. 6 and 7.

Figure 8:
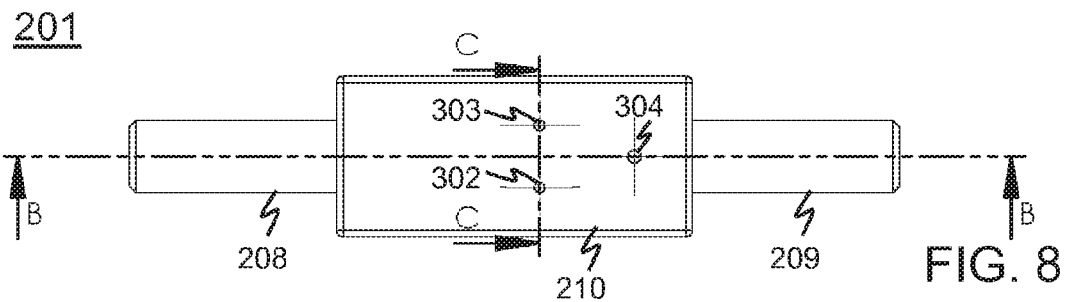
FIG. 8 is a schematic top view of the gas flow passage module in which a (longitudinal) cut line B-B and a (transversal) cut line C-C is indicated.

FIGS. 8 to 11 further schematically illustrate the gas flow passage module 201. FIG. 8 provides a schematic top view of gas flow passage module 201, in FIG. 8, a (longitudinal) cut line B-B and a (transversal) cut line C-C are indicated. The cut line B-B corresponds with the longitudinal symmetry axis mentioned hereinbefore. The third pressure tap 304 is located on this axis. The first and second pressure taps 302, 303 are located on the cut line C-C and symmetrically with respect to the cut line B-B. The cut line C-C may be perpendicular to the cut line B-B.

Figure 9:
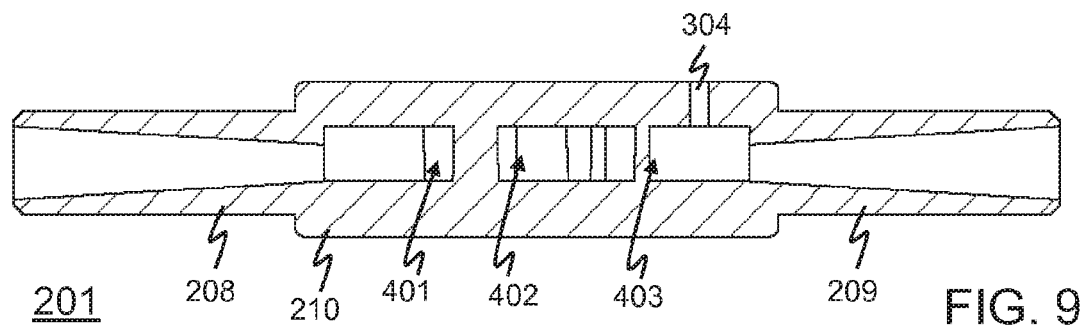
FIG. 9 is a schematic cut view of the gas flow passage module along the cut line B-B indicated in FIG. 8.
Figure 10:
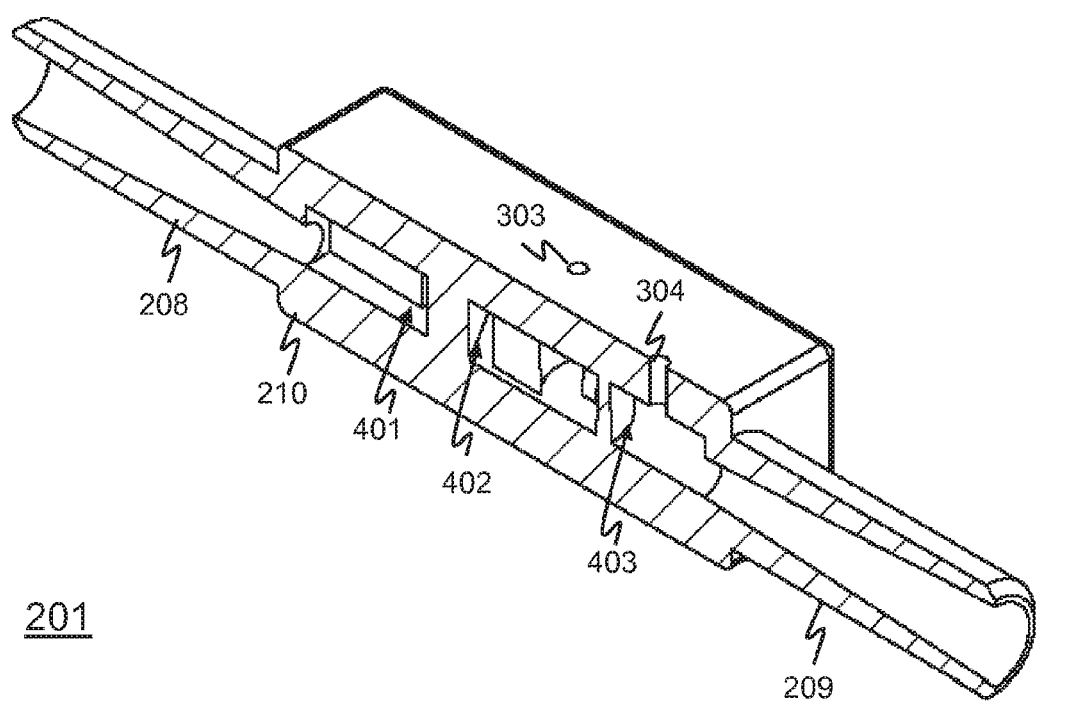
FIG. 10 is a schematic perspective cut view of the gas flow passage module along the cut line B-B indicated in FIG. 8.
Figure 11:
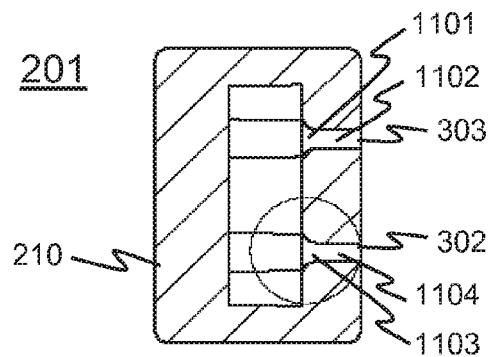
FIG. 11 is a schematic cut view of the gas flow passage module along the cut line C-C indicated in FIG. 8.
Figure 12:
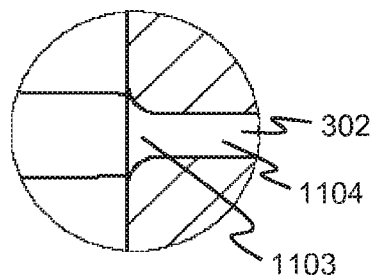
FIG. 12 is an enlargement of a portion of the schematic cut view in FIG. 11, which portion comprises a conduit in the gas flow passage module.

FIG. 9 provides a schematic cut view of the gas flow passage module 20l along the cut line B-B indicated in FIG. 8. FIG. 10 provides a schematic perspective cut view of the gas flow passage module 201 along the cut line B-B indicated in FIG. 8. FIG. 11 provides a schematic cut view of the gas flow passage module 201 along the cut line C-C indicated in FIG. 8. In FIG. 11, a circle indicates a portion of the gas flow passage module 201 that comprises a conduit. FIG. 12 provides an enlargement of this portion indicated in FIG. 11.

FIGS. 11 and 12 illustrate the first and second pressure taps 302, 303 in greater detail. The first pressure tap 302 basically comprises two sections: a conical section 1101 and a section of constant diameter 1102. The conical section 1101 extends from an inner side of the top wall 301 of the gas flow passage module 201 to the section of constant diameter 1102. The section of constant diameter 1102 extends from the conical section 1101 to the outer side of the top wall 301 of the gas flow passage module 201. The second pressure tap 303 is similar to the first pressure tap 302: the second pressure tap 303 also comprises a conical section 1103 and a section of constant diameter 1104.

Figure 13:
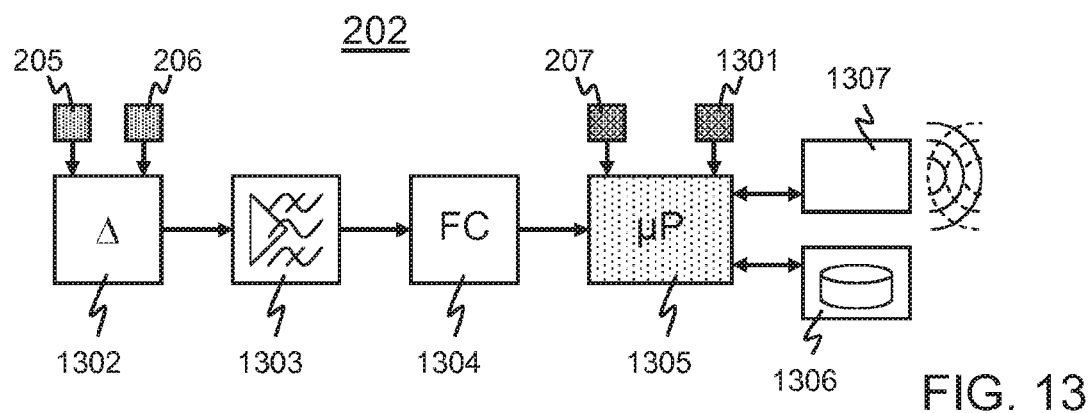
FIG. 13 is a block diagram of a measurement arrangement, which forms part of the oxygen therapy monitoring device.

FIG. 13 schematically illustrates the measurement arrangement 202, which is represented in a block diagram. The measurement arrangement 202 comprises various elements in addition to the acoustic transducers 205, 206 and the pressure sensor 207 already shown in FIG. 2 and discussed hereinbefore. These elements include an ambient pressure sensor 1301, a differential circuit 1302, a signal conditioning circuit 1303, a frequency measurement circuit 1304, a processor 1305, a memory circuit 1306, and a communication interface 1307. As mentioned hereinbefore, these elements may receive electrical power, which is required for their operation, from a battery that may be included in the oxygen therapy monitoring device 105.

The oxygen therapy monitoring device 105 illustrated in FIG. 2, which includes the gas flow passage module 201 illustrated in FIGS. 3 to 12, basically operates as follows. Referring to FIG. 1, gas flow passage module 201 receives the gas flow from the gas source 102. Referring to FIGS. 3 to 5, the gas flow enters into the flow conditioner 401 through the inlet connector 208. The flow conditioner 401 creates a relatively stable airflow profile without causing a significant pressure loss. The gas flow that enters through the inlet connector 208 will typically have a non-uniform velocity profile. The velocity profile will typically have a parabolic shape, which favors flow instability. The flow conditioner 401 reduces this disparity in velocity and stabilizes the gas flow. In effect, the gas flow hits the largest side of the triangularly shaped element 601 clearly shown in FIGS. 6 and 7 and then divides into two equivalent flows, whereby each flow is accelerated in a constant manner. The two flows join at the obtuse angle of the triangularly shaped element 601. At this point, the gas flow has a substantially uniform, flat velocity profile essentially flat, which makes the gas flow stable.

The nozzle 402 accelerates the gas flow that leaves the flow conditioner 401. This accelerated version of the gas flow constitutes a jet that is substantially free of any vortices. The nozzle 102 injects this jet into the oscillation chamber 403.

The oscillation chamber 403 induces an oscillation in the gas flow that enters into the oscillation chamber 403 as a jet. This oscillation is induced by a physical phenomenon that is commonly referred to as the Coanda effect. Two vortices are formed, one vortex on one side of the jet that enters into the oscillation chamber 403, the other vortex on another side of the jet. The two vortices are in counter rotation with respect to each other: one rotates clock-wise: the other vortex rotates counter clock-wise. Each vortex is alternately strong and weak, whereby the vortices are in phase opposition with respect to each other. These out-of-phase varying vortices interact with the jet. This makes the jet oscillate. The oscillation has a frequency, or period, that varies as a function of the flow rate of the gas flow.

In the oscillation chamber 403 described hereinbefore, the two vortices are constant in size, independently of flow rate. This is an advantageous feature, which allows a substantially linear relation between the flow rate and the frequency at which the jet oscillates. Such a linear relationship facilitates processing in the measurement arrangement 202 and, in addition, contributes to precision, reliability in measuring a breathing characteristic and thus in monitoring the oxygen therapy that is applied to the person 101, as illustrated in FIG. 1.

The oscillation in the gas flow, which is the jet in oscillation chamber 403, causes local pressure variations within the oscillation chamber 403. These local pressure variations are thus representative, of the oscillation in the gas flow. For example, the local pressure variations have the same frequency as that at which the jet oscillates.

Accordingly, local pressure variations will occur at the first location in the vortex inducing section 404 of the oscillation chamber 403 to which the first pressure tap 302 extends. Local pressure variations will also occur at the second location to which the second pressure tap 303 extends. These respective pressure variations are in phase opposition. This is, at least partially, due to the first and second pressure taps 302, 303 being symmetrically located with respect to the longitudinal symmetry axis.

Additionally, the first and second pressure taps 302, 303 are preferably located so that the two vortices follow a regular pattern over time. CFD simulations may assist in determining appropriate locations for the first and second pressure taps 302, 303, thereby determining the first and second location in the vortex inducing section 404 of the oscillation chamber 403. CFD is an acronym of "Computational Fluid Dynamics".

The gas flow exits the oscillation chamber 403 through its output section 405. The gas flow then passes through the outlet connector 209 of the gas flow passage module 201.

The measurement arrangement 202 can determine the flow rate on the basis of the oscillation that is induced in the gas flow, which is reflected in the aforementioned local pressure variations. Basically, an oscillation period entails a passage of a volume of gas through the oscillation chamber 403. This volume of passing gas will be designated as "digital volume" hereinafter. The digital volume is related to the volume of the oscillation chamber 403, both having the same order of magnitude. The flow rate can be determined by dividing the digital volume by the oscillation period. The oscillation period may be determined by means of a frequency measurement that extends over a certain time interval. The oscillation period is the inverse of the frequency that is measured.

In more detail, the first acoustic transducer 205 of the measurement arrangement 202 measures the local pressure variations that occur at the first location of the oscillation chamber 403. This is because the first pressure tap 302 and the first bore in the printed circuit board 203 jointly constitute a conduit, which transfers these local pressure variations to the first acoustic transducer 205. In this conduit, the conical section of the first pressure tap 302 provides an acoustic impedance transformation. This acoustic impedance transformation may contribute to sensitivity and precision in measuring the local pressure variations that occur at the first location.

Similarly, the second acoustic transducer 206 measures the local pressure variations that occur at the second location of the oscillation chamber 403. The second pressure tap 303 and the second bore in the printed circuit board 203 jointly constitute a further conduit, which transfers these local pressure variations to the second acoustic transducer 206. In this conduit, the conical section of the second pressure tap 303 provides an acoustic impedance transformation, which may contribute to sensitivity and precision as mentioned hereinbefore.

The first and second acoustic transducers 205, 206 thus provide respective output signals that are representative of the respective pressure variations at the first and second locations, respectively, in the oscillation chamber 403. Since these respective pressure variations are in phase opposition, the respective output signals of the first and second acoustic transducers 205, 206 are also in phase opposition.

The first and second acoustic transducers 205, 206 may be relatively sensitive so that the pressure variations at the first and second locations, respectively, cause saturation within these sensors. That is, the pressure variations cause the respective outputs signals of the first and second acoustic transducers 205, 206 to reach maximum and minimum values. In this case, the respective output signals of these sensors are of a digital nature, which may facilitate their processing. It should be noted that the use of acoustic sensors for measuring the pressure variations, rather than conventional pressure sensors, allow determining the flow rate at a relatively high sample rate and with relatively high precision.

The differential circuit 1302 provides an output signal that represents a difference between the respective output signals of the first and second acoustic transducers 205, 206. Accordingly, the output signal of the differential circuit 1302 is representative of a differential between the respective pressure variations that occur at the first and second locations in the oscillation chamber 403. Such a differential measurement allows suppression of common mode noise, which contributes to measurement sensitivity and reliability. This measurement scheme is also relatively robust: it is possible to determine the flow rate even in the case one of two vortices is missing and, consequently, pressure variations occur at one the two locations only.

The signal conditioning circuit 1303 may apply a low pass filtering to the output signal of the differential circuit 1302, as well as a high pass filtering. The low pass filtering may suppress low frequency noise due to, for example, pressure drift. The high pass filtering may suppress high frequency noise due to, for example, pressure turbulences and exterior acoustic noises. The signal conditioning circuit 1303 may further amplify the output signal of the differential circuit 1302, or a filtered version thereof. The signal conditioning circuit 1303 provides a processed version of the output signal of the differential circuit 1302. This output signal comprises pulses that occur at a frequency corresponding with the frequency at which the gas flow oscillates. In fact, a pulse corresponds with an oscillation period in the gas flow.

The frequency measurement circuit 1304 measures the frequency of the pulses in the output signal of the signal conditioning circuit 1303. The frequency measurement circuit 1304 thus measures the frequency at which the gas flow oscillates. To that end, the frequency measurement circuit 1304 may count a number of pulses that occur during a measurement time interval. The number of pulses that have been counted are indicative of an average frequency at which the gas flow oscillates during the measurement time interval concerned. The average frequency that is actually measured will nonetheless be regarded as an instantaneous frequency, which applies to a particularly positioned instant in the measurement time interval. This is for reasons of convenience and simplicity.

The frequency measurement circuit 1304 may repetitively carry out an instantaneous frequency measurement as described hereinbefore at a rate, which will be referred to as sampling rate hereinafter. Accordingly, the frequency measurement circuit 1304 may provide successive frequency count values at the sampling rate. A frequency count value having a sequence number n, n being an integer, represents the instantaneous frequency at which the gas flow oscillates at an instant $t_n$, which is comprised in the measurement time interval concerned.

The processor 1305 may convert a frequency count value into a flow rate measurement value. To that end, the processor 1305 may multiply the frequency count value by a conversion factor. The conversion factor can be determined from the digital volume and the length of the measurement time interval. A unit in the count value represents a quantity of gas corresponding with the digital volume. Consequently, if the frequency count value is N, N being an integer, this implies that N times the digital volume has flowed through the gas passage module during the measurement time interval. The conversion factor may thus be calculated as being equal to the digital volume divided by the measurement time interval. The conversion factor may also be determined by means of calibration. For example, a gas flow may be passed through the gas passage module at various different know, predefined flow rates. This will produce respective different frequency count values from which the conversion factor can be determined.

Accordingly, the processor 1305 calculates successive instantaneous flow rates from of the successive frequency count values, which the frequency measurement circuit 1304 provides. An instantaneous flow rate having the sequence number n is calculated from the frequency count value having the same sequence number. This instantaneous flow rate applies to the instant $t_n$, which is comprised in the measurement time interval for which this frequency count was obtained.

The pressure sensor 207 may measure a pressure of the gas flow in the output section 405 of the oscillation chamber 403. The pressure sensor 207 may repetitively carry out this pressure measurement at the sampling rate mentioned hereinbefore. Accordingly, the pressure sensor 207 may provide successive instantaneous pressure values at the sampling rate. The processor 1305 may receive these successive instantaneous pressure values. An instantaneous pressure value indicates a pressure of the gas flow in the output section 405 of the oscillation chamber 403 at an instant when the pressure measurement concerned was carried out.

The ambient pressure sensor 1301 may measure an ambient pressure in a space where the system 100 illustrated in FIG. 1 operates. Similarly, the ambient pressure sensor 1301 may repetitively carry out this ambient pressure measurement at the sampling rate mentioned hereinbefore. Accordingly, the ambient pressure sensor 1301 may provide successive instantaneous ambient pressure values at the sampling rate. The processor 1305 may receive this successive instantaneous pressure values. An instantaneous ambient pressure value indicates a pressure of ambient air in the space where the system 100 operates at an instant when the ambient pressure measurement concerned was carried out.

The processor 1305 may derive information from the successive instantaneous flow rates that have been measured, as well as from the successive instantaneous pressure values and the successive instantaneous ambient pressure values. This will be described in greater detail hereinafter. The aforementioned measurement data may be stored, at least temporarily, in the memory circuit 1306 of the measurement arrangement 202 illustrated in FIG. 13. This storage may be for a purpose of later analysis, or archiving, or both. The measurement data may be communicated to the in-situ station 107 illustrated in FIG. 1 through the communication interface 1307 of the measurement arrangement 202 illustrated in FIG. 13. This equally applies to data that the processor 1305 may obtain by processing the measurement data, as will be described hereinafter.

The following considerations underlie some particular features of the oxygen therapy monitoring device 105 within the system 100 illustrated in FIG. 1. The sampling rate may be relatively high because it may be desired to detect relatively short-term variations in the flow rate of the gas flow. For example, a breathing pattern that is relatively fast may comprise 30 breaths per minute, which corresponds to a frequency of 0.5 Hz. This breathing pattern can satisfactorily be measured if, for example, the sampling rate is 5, which implies that 5 instantaneous frequency measurements are carried out per second. This further implies that successive measurement time intervals should each have a length not exceeding 0.2 seconds (200 ms).

The gas flow should oscillate at a relatively high frequency in order to detect relatively small variations in the flow rate of the gas flow. This is because there is a rounding error in a pulse count that the frequency measurement circuit 1304 carries out. The higher the number of pulses is that are counted during a measurement time interval, the smaller than rounding error is. For example, in case 10 pulses are counted in an instantaneous frequency measurement, the rounding error can reach 5%. This is then also an imprecision in the instantaneous flow rate that is measured on the basis of this pulse count. The higher the frequency is at which the gas flow oscillates, the higher the number of pulses is that are counted during a measurement time interval and, consequently, the smaller the imprecision is in the instantaneous flow rate that is measured.

The following is a numerical example that may apply to the oxygen therapy monitoring device 105 within the system 100 illustrated in FIG. 2. The sampling rate is 5, as mentioned hereinbefore, so that a pulse count spans a time interval of 0.2 seconds at the most. Instantaneous flow rates should be measured with a resolution of at least 5%, which is equivalent to 5% imprecision. This implies a count of at least 10 pulses during the time interval of 0.2 seconds. Since a pulse corresponds with an oscillation period of the gas flow in the oscillation chamber 403, this in turn implies that the gas flow should oscillate at a frequency of at least 50 Hz. This numerical example shows that the acoustic sensors of the measurement arrangement 202 may functionally be regarded as microphones.

The volume of the oscillation chamber 403 is relatively small so that the gas flow oscillates at a sufficiently high frequency within a flow rate range of interest. In this system 100 illustrated in FIG. 1, the flow rate range of interest may be comprised between 0.5 L per minute and 10 L per minute. The gas flow oscillates at a lowest frequency at a lower boundary of the flow rate range, which is 0.5 L per minute in this example. Based on the numerical example hereinbefore, the gas flow should oscillate at a frequency of at least 50 Hz at this lower boundary flow rate. As explained hereinbefore, one oscillation period involves an amount of gas passing through the oscillation chamber 403, the digital volume, which relates to the volume of the oscillation chamber 403. A frequency of at least 50 Hz, at a flow rate of 0.5 L per minute, implies that at least 3000 times the digital volume should not exceed 0.5 L. Consequently, assuming that the digital volume is precisely equal to the volume of the oscillation chamber 403 should not exceed 0.5 L divided by 3000, which division is equal to 166 cubic millimeters ($mm^3$).

Such a relatively small oscillation chamber 403 may introduce a relatively significant pressure loss. For example, the oscillation chamber 403 that has a volume of about 100 to 200 $mm^{-3}$ may introduce a pressure loss as high as 1000 Pa at a flow rate of 10 liters per minute. This relatively high pressure loss may be acceptable in the system 100 illustrated in FIG. 1 if, for example, requirements are relatively relaxed concerning a pressure that the gas flow should have in the mask 106.

Figure 14:
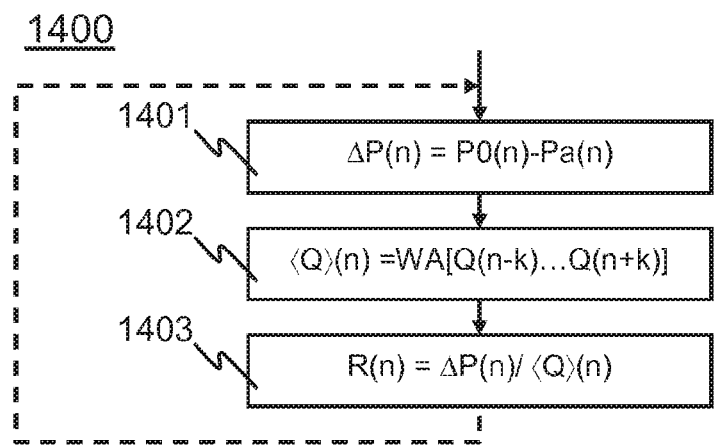
FIG. 14 is a flow chart diagram of a non therapeutic method (1400) of monitoring an oxygen therapy applied to a person.

FIG. 14 schematically illustrates a non therapeutic method 1400 of monitoring an oxygen therapy applied to a person. The method 1400 is illustrated in a flow chart. The method 1400 comprises a series of steps, which the processor 1305 in the measurement arrangement 202 may carry out in cooperation with other elements. The flow chart can be regarded as a representation of a software program that has been installed in the processor 1305, or another circuit associated with the processor 1305.

In an overpressure calculation step 1401, the processor 1305 calculates an instantaneous overpressure value from a difference between an instantaneous pressure value and an instantaneous ambient pressure value, which the pressure sensor 207 and the ambient pressure sensor 1301 have provided, respectively. The aforementioned values apply to the same instant and have therefore the same sequence number. The instantaneous overpressure value represents an overpressure at the instant concerned between the gas flow that is applied to the mask 106 and the ambient pressure in the space where the system 100 illustrated in FIG. 1 operates.

In a sliding average flow rate calculation step 1402, the processor 1305 calculates an instantaneous average of the flow rate of the gas flow. The instantaneous average of the flow rate applies to the same instant as that to which the instantaneous overpressure value applies. The instantaneous average of the flow rate is obtained by a weighted average of the instantaneous flow rate at that instant, a number k of preceding instantaneous flow rates, and the same number k of subsequent instantaneous flow rates, k being an integer. This weighted average calculation can be regarded as a zero delay filter operation over 2k+1 instantaneous flow rates that have been measured. This filter operation further suppresses noise that may affect instantaneous flow rates measurements.

In a resistance calculation step 1403, the processor 1305 divides the instantaneous overpressure value by the instantaneous average of the flow rate of the gas flow. These values thus relate to the same instant. This division produces a characteristic value that may be regarded as representing a "resistance" at the level of the mask 106 illustrated in FIG. 1. In case the gas flow that reaches the mask 106 has a relatively high overpressure, whereas the flow rate is relatively low, there is a relatively high resistance at the level of the mask 106. Conversely, in case the gas flow that reaches the mask 106 has a relatively low overpressure, whereas the flow rate is relatively high, there is a relatively low resistance at the level of the mask 106. The characteristic value that the division produces in this step will hereinafter be referred to as resistance value for reasons of convenience and clarity. An interesting aspect of the resistance value is that characteristics of the gas source 102 do not substantially affect this value. This independency on gas source 102 characteristics contributes to ease-of-use and reliability.

The processor 1305 may repetitively carry out the series of steps illustrated in FIG. 14, which have been described hereinbefore. In doing so, the processor 1305 produces a sequence of successive resistance values, whereby a resistance value is associated with a particular instant. The processor 1305 may then determine a breathing characteristic on the basis of the sequence of successive resistance values. For example, the processor 1305 may determine a breathing frequency and variations in the breathing frequency. In general, the processor 1305 may extract valuable information from the sequence of successive resistance values, in particular information on the breathing of the person 101 in the system 100 illustrated in FIG. 1. The processor 1305 may further detect anomalies in this system 100 on the basis of the sequence of successive resistance values.

Figure 15:
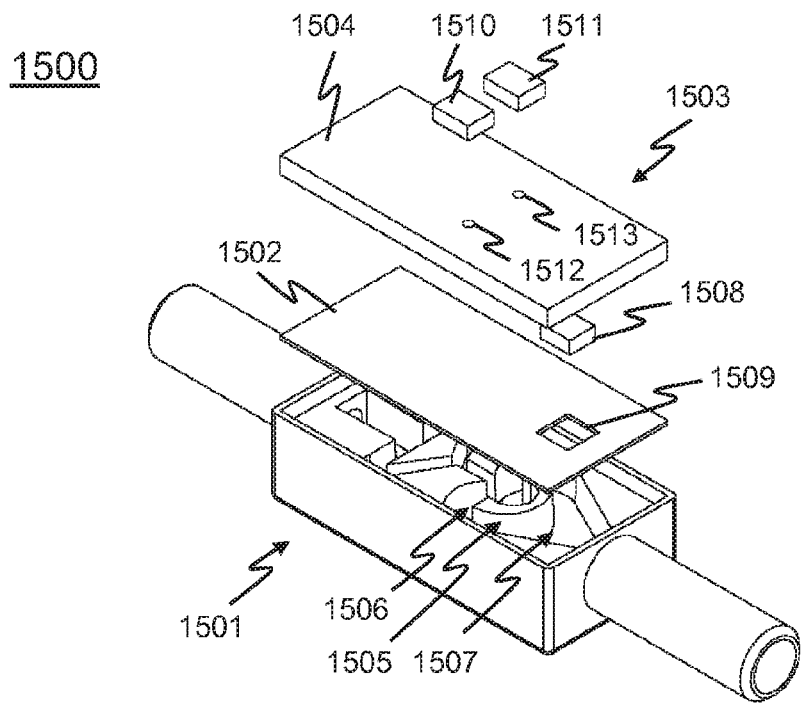
FIG. 15 is a schematic exploded perspective view of an alternative oxygen therapy monitoring device.

FIG. 15 schematically illustrates an alternative oxygen therapy monitoring device 1500. FIG. 15 provides a schematic exploded perspective view of the alternative oxygen therapy monitoring device 1500. The alternative oxygen therapy monitoring device 1500 comprises an alternative gas flow passage module 1501, an alternative acoustically transparent membrane 1502, and an alternative measurement arrangement 1503, which may be implemented on an alternative printed circuit board 1504, as illustrated in FIG. 15. The alternative oxygen therapy monitoring device 1500 may be used in the system 100 illustrated in FIG. 1, replacing the oxygen therapy monitoring device 105 illustrated in FIG. 3 described hereinbefore in detail. The alternative oxygen therapy monitoring device 1500 may also operate in a fashion similar to that in which the oxygen therapy monitoring device 105 illustrated in FIG. 3 operates. Differences are primarily of a structural nature.

The alternative gas flow passage module 1501 has an open top side, whereas the gas flow passage module 201 illustrated in FIG. 2 comprises a top wall 301. The alternative printed circuit board 1504 functionally replaces the top wall 301. That is, alternative printed circuit board 1504 seals the alternative gas flow passage module 1501, together with the alternative acoustically transparent membrane 1502, which is disposed between the aforementioned parts. The alternative gas flow passage module 1501 may have an inner structure similar to that of the gas flow passage module 201 illustrated in FIG. 3, which has been described in detail hereinbefore. The alternative gas flow passage module 1501 may thus comprise an oscillation chamber 1505 having a vortex-inducing section 1506 and an output section 1507.

The alternative measurement arrangement 1503 comprises a pressure sensor 1508 that is mounted on a bottom side of the alternative printed circuit board 1504, rather than on a top side as in the oxygen therapy monitoring device 105 illustrated in FIG. 2. The alternative acoustically transparent membrane 1502 comprises an opening 1509 for the pressure sensor 1508. The pressure sensor 1508 may thus at least partially extend in the output section 1507 of the oscillation chamber 1505. The alternative measurement arrangement 1503 further comprises a pair of acoustic transducers 1510, 1511, which may be mounted on the top side of the alternative printed circuit board 1504. This mounting may be similar to that of the pair of acoustic transducers 205, 206 on the printed circuit board 203 in the oxygen therapy monitoring device 105 illustrated in FIG. 2.

The alternative printed circuit board 1504 comprises two bores 1512, 1513 associated with the pair of acoustic transducers 1510, 1511. One of the bores 1512 provides pressure communication between one of the acoustic transducers 1510 and the oscillation chamber 1505, more precisely, a first location in the oscillation chamber 1505. The other bore 1513 provides pressure communication between the other acoustic transducer 1511 and the oscillation chamber 1505, more precisely, a second location in the oscillation chamber 1505. In this respect, the printed circuit board 203 in the oxygen therapy monitoring device 105 illustrated in FIG. 2 and the alternative printed circuit board 1504 in the alternative oxygen therapy monitoring device 1500 illustrated in FIG. 15 may be similar.

Notes

The detailed description hereinbefore with reference to the drawings is merely an illustration of the invention and the additional features, which are defined in the claims. The invention can be implemented in numerous different ways. In order to illustrate this, some alternatives are briefly indicated.

The invention may be applied in numerous types of products or methods related to measuring or measuring breathing of a living being. For example, the invention may, in principle, be applied in any type of method wherein breathable gas is applied to a living being. The expression "measuring a breathing characteristic" should be understood in a broad sense. The expression may embrace any operation aiming at obtain data related to the breathing of a living being.

The invention may be implemented in numerous manners. For example, in an alternative embodiment, a differential acoustic sensor may replace the pair of acoustic sensors illustrated in FIGS. 2 and 13. In such an alternative embodiment, the differential circuit 1302 illustrated in FIG. 13 may be dispensed with.

The term "oscillation chamber" should be understood in a broad sense. The term may embrace any constructed space having an interior shape arranged to induce pressure variations in an airflow that passes through the oscillation chamber, whereby these pressure variations exhibit a frequency that is a monotonous function of a flow rate of the airflow passing through the oscillation chamber.

An oscillation chamber may be implemented in numerous different ways. In alterative embodiments, the oscillation chamber may comprise a gas flow obstructing element different from, that in the embodiment illustrated in FIG. 5. The oscillation chamber may also have an open configuration, without a gas flow obstructing element. A flow conditioner may be implemented in numerous different ways. In alterative embodiments, the flow conditioner may comprise, for example, grids or blades, have a honeycomb structure or another structure.

It should be noted that the method illustrated in FIG. 14 does not necessarily require an oxygen therapy monitoring device as described hereinbefore, which measures the flow rate on the basis of an oscillation induced in a gas flow. In principle, the method can be used in any system in which breathable gas is applied to a living being through a breathing interface. What matters is that an overpressure of the gas flow at the breathing interface is measured, or estimated, and that a resistance value is calculated by dividing the overpressure by the flow rate of the gas flow. In this respect, it does not matter how the flow rate is actually measured.

In general, there are numerous different ways of implementing the invention, whereby different implementations may have different topologies. In any given topology, a single module may carry out several functions, or several modules may jointly carry out a single function. In this respect, the drawings are very diagrammatic. There are numerous functions that may be implemented by means of hardware or software, or a combination of both. A description of a software-based implementation does not exclude a hardware-based implementation, and vice versa. Hybrid implementations, which comprise one or more dedicated circuits as well as one or more suitably programmed processors, are also possible. For example, various functions described hereinbefore with reference to the figures may be implemented by means of one or more dedicated circuits, whereby a particular circuit topology defines a particular function.

There are numerous ways of storing and distributing a set of instructions, that is, software, which allows monitoring an oxygen therapy applied to a person. For example, software may be stored in a suitable device readable medium, such as, for example, a memory circuit, a magnetic disk, or an optical disk. A device readable medium in which software is stored may be supplied as an individual product or together with another product, which may execute the software. Such a medium may also be part of a product that enables software to be executed. Software may also be distributed via communication networks, which may be wired, wireless, or hybrid. For example, software may be distributed via the Internet. Software may be made available for download by means of a server. Downloading may be subject to a payment.

The remarks made hereinbefore demonstrate that the detailed description with reference to the drawings is an illustration of the invention rather than a limitation. The invention can be implemented in numerous alternative ways that are within the scope of the appended claims. All changes that come within the meaning and range of equivalency of the claims are to be embraced within their scope. Any reference sign in a claim should not be construed as limiting the claim. The word "comprising" does not exclude the presence of other elements or steps than those listed in a claim. The word "a" or "an" preceding an element or step does not exclude the presence of a plurality of such elements or steps. The mere fact that respective dependent claims define respective additional features, does not exclude combinations of additional features other than those reflected in the claims.

The invention claimed is:

1. An oxygen therapy monitoring device comprising:
   a gas flow path adapted to pass a gas flow from a source to a breathing interface for a person, the gas flow path having various successive sections from an inlet connector to an outlet connector, these sections including:
   a flow conditioner;
   a nozzle; and
   an oscillation chamber adapted to induce an oscillation in the gas flow that varies as a function of a flow rate of the gas flow, the oscillation chamber having a volume smaller than 1000 mm$^3$; and
   a measurement arrangement adapted to measure the oscillation induced in the gas flow and to determine the flow rate on the basis of the oscillation that is measured.

2. An oxygen therapy monitoring device according to claim 1, wherein the measurement arrangement is adapted to measure pressure variations in the oscillation chamber caused by the oscillation and to determine the flow rate on the basis of the pressure variations that are measured.

3. An oxygen therapy monitoring device according to claim 2, wherein the measurement arrangement is coupled to receive pressure variations that occur at one location in the oscillation chamber and pressure variations that occur at another location in the oscillation chamber, the measurement arrangement being adapted to determine the flow rate on the basis of a differential between these respective pressure variations.

4. An oxygen therapy monitoring device according to claim 3, wherein the measurement arrangement is coupled to the oscillation chamber so that the respective pressure variations at the one and the other location that the measurement arrangement receives are in phase opposition.

5. An oxygen therapy monitoring device according to claim 2, further comprising at least one conduit adapted to transfer the pressure variations that occur at a location in the oscillation chamber to the measurement arrangement, the conduit being adapted to provide an acoustic impedance transformation.

6. An oxygen therapy monitoring device according to claim 1, wherein the oscillation chamber comprises a gas flow obstacle element that defines a cavity facing an inlet through which the gas flow enters the oscillation chamber.

7. An oxygen therapy monitoring device according to claim 1, further comprising a pressure sensor adapted to measure a pressure of the gas flow.

8. An oxygen therapy monitoring system comprising an oxygen therapy monitoring device according to claim 1, and a station adapted to collect measured data from the oxygen therapy monitoring device.

9. A non therapeutic method of monitoring an oxygen therapy applied to a person, the non therapeutic method comprising a step of collecting measured data from an oxygen therapy monitoring device according to claim 1.

10. A non therapeutic method according to claim 9, wherein the device repetitively carries out the following series of operations:
    measuring an overpressure of the gas flow at the breathing interface; and
    calculating a resistance value by dividing the overpressure by the flow rate of the gas flow; and
    in addition to the series of operations,
    determining a breathing characteristic on the basis of a sequence of successive resistance values that has been obtained.

* * * * *